United States Patent

Furukawa et al.

[11] Patent Number: 4,717,728
[45] Date of Patent: Jan. 5, 1988

[54] CYCLIC AMIDINYL AND CYCLIC GUANIDINYL THIO CARBAPENEMS

[75] Inventors: Minoru Furukawa, Ichikawa; Makoto Sato, Funabashi, both of Japan

[73] Assignee: Merck & Co., Inc., Rahway, N.J.

[21] Appl. No.: 553,609

[22] Filed: Nov. 21, 1983

[51] Int. Cl.$^4$ .................. C07D 487/04; A61K 31/395
[52] U.S. Cl. ..................................... 514/210; 540/350
[58] Field of Search ................. 260/245.2 R, 245.2 T; 424/270, 271; 540/350; 514/210

[56] References Cited

U.S. PATENT DOCUMENTS

| | | | |
|---|---|---|---|
| 4,410,533 | 10/1983 | Ponsford et al. | 260/245.2 T |
| 4,473,578 | 9/1984 | Corbett | 260/245.2 R |
| 4,477,662 | 10/1984 | Corbett et al. | 260/245.2 R |
| 4,552,873 | 11/1983 | Miyaka et al. | 260/245.2 T |

*Primary Examiner*—Nicholas S. Rizzo
*Attorney, Agent, or Firm*—Raymond M. Speer; Hesna J. Pfeiffer

[57] ABSTRACT

Compounds of the formula:

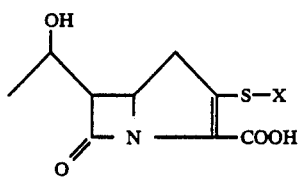

and the pharmaceutically acceptable salts thereof wherein X is

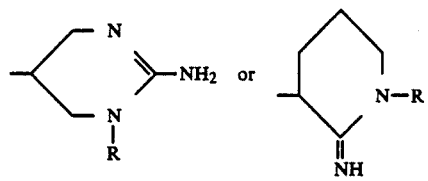

wherein each R is hydrogen or alkyl of 1 to 6 carbon atoms are disclosed. The compounds are useful as antibiotics.

5 Claims, No Drawings

CYCLIC AMIDINYL AND CYCLIC GUANIDINYL THIO CARBAPENEMS

The present invention relates to cyclic amidinyl and cyclic guanidinyl thio carbapenems. These compounds are useful as antibiotics. The present invention also relates to processes for preparing these compounds.

There is a continuing need for new antibiotics. Unfortunately, continued wide scale use of an antibiotic often gives rise to resistant strains of pathogens. In addition, the known antibiotics suffer from the disadvantage of being effective only against certain types of microorganisms. Accordingly, the search for new antibiotics continues.

The compounds of the present invention are compounds of the formula:

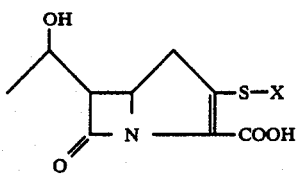

and the pharmaceutically acceptable salts thereof wherein X is

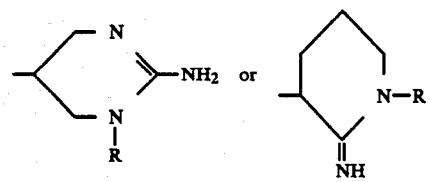

wherein each R is hydrogen or alkyl of 1 to 6 carbon atoms.

One embodiment of the present invention relates to compounds of the formula

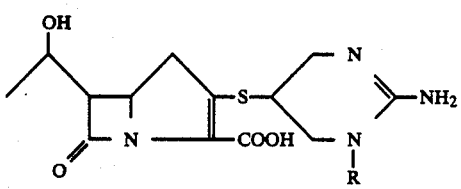

and the pharmaceutically acceptable salts thereof wherein R is hydrogen or alkyl of 1 to 6 carbon atoms. Compounds where R is hydrogen are preferred.

A second embodiment of the present invention relates to compounds of the formula

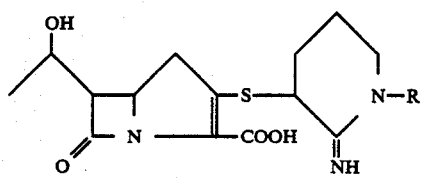

and the pharmaceutically acceptable salts wherein R is hydrogen or alkyl of 1 to 6 carbon atoms. Compounds where R is hydrogen are preferred.

The following compounds are representative of the compounds of the present invention:

2-[2-amino-3,4,5,6-tetrahydropyrimidin-5-yl)thio]-6-(1-hydroxymethyl)-1-carbadethiapen-2-em-3-carboxylic acid;

2-[2-amino-1-methyl-1,4,5,6-tetrahydropyrimidin-5-yl)thio]-6-(1-hydroxyethyl)-1-carbadethiapen-2-em-3-carboxylic acid;

6-(1-hydroxyethyl)-2-(2-iminopiperidin-3-yl)thio-1-carbadethiapen-2-em-3-carboxylic acid;

6-(1-hydroxyethyl)-2-(2-imino-1-methylpiperidin-3-yl)thio-1-carbadethiapen-2-em-3-carboxylic acid.

The products of this invention form a wide variety of pharmaceutically acceptable salts such as acid addition salts, e.g., with hydrochloric, hydrobromic, sulfuric, nitric, toluene-p-sulfonic and methane sulfonic acids. The salts of this invention are pharmaceutically acceptable non-toxic derivatives which can be used as the active ingredient in suitable unit-dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention may therefore be used as antibacterial drugs for treating infections caused by gram-positive or gram-negative bacteria, for example, against *Staphylococcus aureus*, *Escherichia coli*, *Klebsiella pneumoniae*, *Bacillus subtilis*, *Serratia*, *Salmonella typhosa*, *Pseudomonas* and *Bacterium proteus*. The antibacterials of the invention may further be utilized as additives to animal feeds, for preserving foodstuffs and as disinfectants. For example, they may be employed in aqueous compositions in concentrations ranging from 0.1 to 100 parts of antibiotic per million parts of solution in order to destroy and inhibit one growth of harmful bacteria on medical and dental equipment and as bactericides in industrial applications, for example, in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, topically or parenterally by injection (intravenously or intramuscularly)

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, corn starch, calcium phosphate, sorbitol or glycine; lubricants, for example, magnesium stearate, talc, polyethylene glycol, silica; disintegrants, for example, potato starch, or acceptable wetting agents such as sodium lauryl sulfate. The tablets may be coated according to methods well known in the art. Oral liquid preparations may be in the form of aqueous or oily suspensions, solutions, emulsions, syrups, elixirs, etc. or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example, methyl or propyl p-hydroxybenzoates or sorbic acid. Suppositories will contain conventional suppository base, e.g. cocoa butter or other glycerides.

Compositions for injection may be presented in unit dose form in ampules, or in multidose containers with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition and size of the subject being treated as well as the route and frequency of administration, the parenteral route being preferred for generalized infections and the oral route for intestinal infections. Another factor influencing the precise dosage regimen, apart from the nature of the infection and peculiar identity of the individual being treated, is the molecular weight of the chosen species of this invention. In general, a daily oral dosage consists of from about 2 to about 600 mg of active ingredient per kg of body weight of the subject in one or more applications per day. A preferred daily dosage for adult humans lies in the range of from about 15 to 150 mg of active ingredient per kg of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10 to 60%. The composition will generally contain from about 15 mg to about 1500 mg of the active ingredient; however, in general, it is preferable to employ a dosage amount in the range of from about 100 mg to 1000 mg. In parenteral administration the unit dosage is usually the pure compound in a sterile water solution or in the form of a soluble powder intended for solution. Consideration of individual properties of solubility and stability will determine the optimum pH of such a solution. The pH will generally be in range of 5.5 to 8.2.

The following Examples illustrate but do not limit the product, process, compositional or method of treatment aspect of the present invention. All temperatures are in °C.

EXAMPLE 1

A.
1-t-Butoxycarbonylaminomethyl-2-t-butoxycarbonylaminoethanol (2)

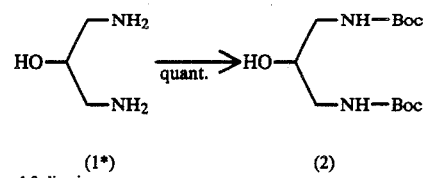

(1*)          (2)
*2-hydroxy-1,3-diaminopropane

To a stirred solution of (1) (3.0 g, 33 mmol) in dioxane (25 ml) and water (7 ml) was added Boc—ON (17.2 g, 70 mmol) at room temperature. After stirring for 1 hr* at room temperature, the reaction mixture was diluted with CHCl$_3$. The separated organic layer was washed with 1N NaOH, water and brine successively, and dried over MgSO$_4$. Evaporation of the solvents gave a residue, which was purified by silica gel column chromatography using CHCl$_3$—MeOH (49:1) to afford (2) (9.6 g, 100%) as a powder.
**2-(tert-butoxycarbonyloximino)-2-phenylacetonitrile
***hour NMR δ(CDCl$_3$): 1.44 [18H, s, 2×—C(Me)$_3$]; 3.20 [4H, t, —CH$_2$CH(OH)—CH$_2$]; 3.60–4.05 (2H, m, HO-CH<); 5.30 (2H, br, —NHBoc).

B.
1-t-Butoxycarbonylaminomethyl-2-t-butoxycarbonylaminoethyl tosylate (3)

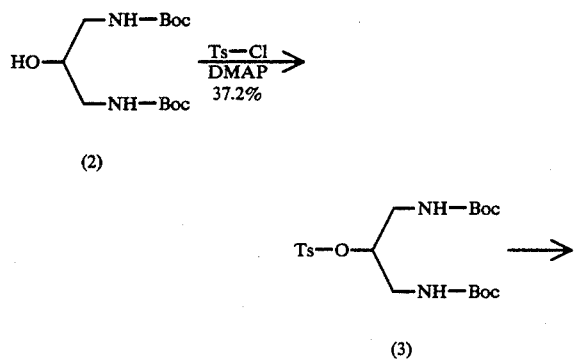

A mixture of (2) (9.40 g, 0.032 mol), TsCl* (11.12 g, 0.058 mol) and DMAP (7.2 g, 0.059 mol) in CHCl$_3$ (100 ml) was heated at 60° for 30 min* under argon. To the reaction mixture were further added TsCl (6.2g, 0.033 mol) and DMAP (1.98 g, 0.016 mol) to complete the reaction and the resulting mixture was heated under reflux for 1 hr under argon. The reaction mixture was diluted with AcOEt**** (300 ml), then washed with 5% HCl, 10% NaHCO$_3$, water and brine, and dried over MgSO$_4$. Evaporation of the solvents gave a residue which was chromatographed on silica gel using 0.5% MeOH—CHCl$_3$ to afford (3) (5.35 g, 37.2%) as a powder.
*p-toluenesulfonyl chloride
**4-dimethylaminopyridine
***minutes

****ethyl acetate

NMR δ(CDCl₃): 1.43 [18H, s, 2×—C(Me)₃]; 2.46 (3H, s, ArMe); 3.00–3.65 [4H, m, TsOCH(CH₂—)₂]; 4.57 [1H, quintet, TsOCH(CH₂—)₂]; 5.00 (2H, br, 2×NHBoc); 7.36 (2H, d, J=9 Hz, 2×ArH); 7.83 (2H, d, J=9 Hz, 2×ArH).

C.
S-[(t-Butoxycarbonylaminomethyl-2-t-butoxycarbonylamino)ethyl]thiobenzoate (4)

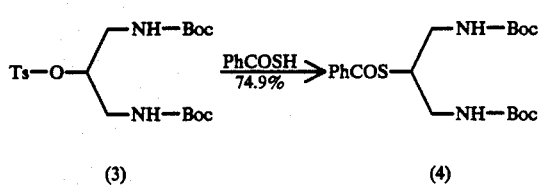

(3)    (4)

A mixture of (3) (4.44 g, 0.01 mol), PhCOSH* (2.76 g, 0.02 mol) and DBU** (3.04 g, 0.02 mol) in benzene (60 ml) was heated under reflux for 1.5 hr. The reaction mixture was diluted with AcOEt (100 ml), washed with 5% NaHCO₃ (5 ml), water (30 ml×2) and brine (30 ml), dried over MgSO₄ and concentrated. The residue was chromatrahed on silica gel using benzene—AcOEt (93:7) to afford (4) (3.07 g, 74.9%) as an oil.

*thiolbenzoic acid
**1,8-diazabicyclo[5.4.0]undecene

NMR δ(CDCl₃): 1.45 [18H, s, 2×C(Me)₃]; 3.10–3.75 [4H, m, PhCOSCH(CH₂—)₂]; 3.90 (1H, quintet, PhCOSCH<); 5.33 (2H, br, 2×NHBoc); 7.30–7.65 (3H, m, 3×ArH); 7.86–8.06 (2H, m, 2×ArH).

D.
1-t-Butoxycarbonylaminomethyl-2-t-butoxycarbonylaminoethanethiol (5)

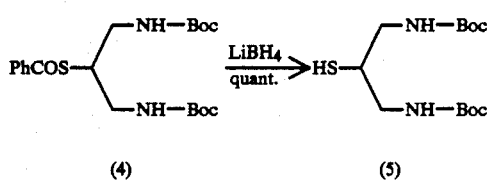

(4)    (5)

To a stirred solution of (4) (3.07 g, 7.5 mmol) in THF* (80 ml) was added LiBH₄ (300 mg, 13.6 mmol) at 0° under argon. After stirring for 40 min at room temperature, excess LiBH₄ was quenched by adding satd. NH₄Cl in an ice bath. The mixture was diluted with AcOEt (150 ml), washed with water (50 ml×3) and brine, dried over MgSO₄ and concentrated. The residue was purified by silica gel column chromatography using benzene—AcOEt (19:1) to give (5) (2.33 g, 100%) as a powder.

*tetrahydrofuran

NMR δ(CDCl₃): 1.43 [18H, s, 2×—C(Me)₃]; 2.80–3.70 [6H, m, HSCH(CH₂—)₂]; 5.46 (2H, br, 2×NHBoc).

E.
1-t-Butoxycarbonylaminomethyl-1-p-methoxybenzylthio-2-t-butoxycarbonylaminoethane (6)

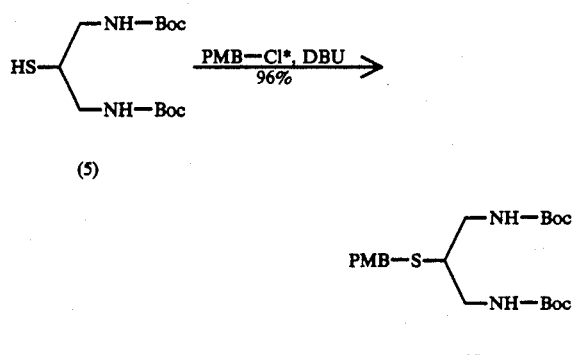

(5)

(6)

*paramethoxybenzylchloride

To a stirred solution of (5) (2.2 g, 7.9 mmol) and PMB—Cl (1.3 g, 8.3 mmol) in benzene (30 ml) was added DBU (1.27 g, 8.3 mmol) at room temperature. After stirring for 2 hr, the reaction mixture was diluted with AcOEt (50 ml), washed with water and brine, then dried over MgSO₄. Evaporation of the solvents gave a residue, which was chromatographed on silica gel using benzene-AcOEt (19:1) to afford (6) (3.25 g, 96.3%) as an oil.

NMR δ(CDCl₃): 1.43 [18H, s, 2×—C(Me)₃]; 2.60–3.55 [5H, m, PMB—s—CH(CH₂—)₂]; 3.74 (3H, s, ArOMe); 4.50–4.70 (2H, m, —CH₂Ar); 6.70–6.95 (2H, m, 2×ArH); 7.10–7.30 (2H, m, 2×ArH).

F. p-Nitrobenzyl Methoxy(thiocarbonyl)carbamate (7)

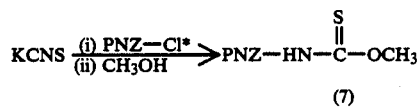

*paranitrobenzylchloroformate

To a stirred solution of KSCN (2.9 g, 0.03 mol) in dry acetone (150 ml) was added a solution of PNZ—Cl (6.8 g, 0.032 mol) in dry acetone (20 ml) under ice-cooling. After stirring for 2 hr in an ice bath, MeOH (1.15 g, 0.036 mol) was added to the reaction mixture, and then the mixture was stirred for 20 hr at room temperature and filtered. The filtrate was concentrated to give a residue, which was triturated with CHCl₃ to give (7) (2.88 g, 35.7%) as a powder.

NMR δ(CDCl₃): 4.03 (3H, s, OMe); 5.33 (2H, s, —CH₂Ar); 7.70 (2H, d, J=9 Hz, 2×ArH); 8.80 (2H, d, J=9 Hz, 2×ArH).

G. p-Nitrobenzyl N-[Methoxy(methylthio)methylene]carbamate (8)

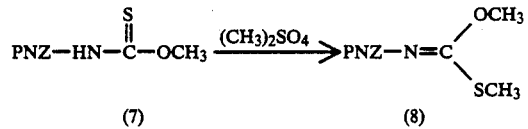

(7)    (8)

To a stirred solution of (7) (3.5 g, 0.013 mol) and K₂CO₃ (1.79 g, 0.013 mol) in dioxane (40 ml) and water (40 ml) was slowly added Me₂SO₄ (1.72 g, 0.014 mol) at room temperature. After stirring for 30 min, K₂CO₃

(300 mg, 2 mmol) and Me$_2$SO$_4$ (300 mg, 2 mmol), was added to the reaction mixture, and stirring was continued for 1.5 hr. The reaction mixture was diluted with AcOEt (200 ml), washed with water and brine, and dried over MgSO$_4$. After evaporation of the solvent, the resultant residue was triturated with n-pentane to afford (8) (3.23 g, 87.8%) as a powder.

NMR δ(DMSO-d$_6$): 2.40 (3H, s, —S$\underline{Me}$); 4.00 (3H, s, —O$\underline{Me}$); 5.28 (2H, s, —C$\underline{H}_2$Ar); 7.56 (2H, d, J=9 Hz, 2×Ar$\underline{H}$); 8.22 (2H, d, J=9 Hz, 2×Ar$\underline{H}$).

H.
2-p-Nitrobenzyloxycarbonylimino-5-p-methoxybenzyl-thiohexahydro-pyrimidine (10)

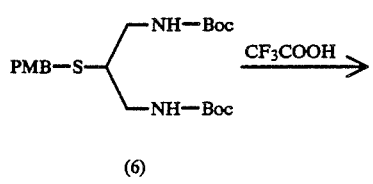

(6)

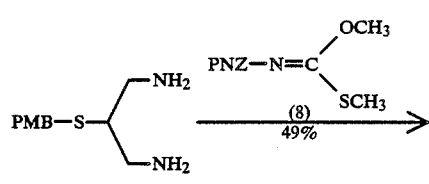

(9)

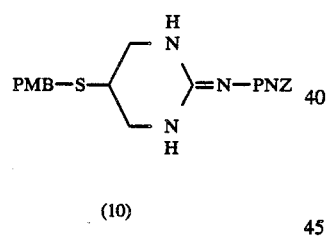

(10)

A mixture of (6) (3.05 g, 7.2 mmol), anisole (8 ml) and CF$_3$CO$_2$H was stirred for 30 min in an ice bath and stirring was continued for 1 hr at room temperature. After evaporation of CF$_3$CO$_2$H under reduced pressure, the residue was dissoluved in water. The aqueous soluiton was washed with n-hexane (20 ml×3), made alkaline by conc.NH$_4$OH, and then extracted with CHCl$_3$ (150 ml×3). The organic layer was dried over MgSO$_4$ and concentrated to give crude (9) (1.13 g) as an oil.

NMR δ(CDCl$_3$): 1.40 (4H, s, 2×—N$\underline{H}_2$); 2.40–3.05 [5H, m, PNB—S—C$\underline{H}$(C$\underline{H}_2$NH$_2$)$_2$]; 3.70 (2H, s, Ar—C$\underline{H}_2$—S—); 3.80 (3H, s, Ar—$\underline{Me}$, ArO$\underline{Me}$); 6.84 (2H, d, J=9 Hz, 2×Ar$\underline{H}$); 7.25 (2H, d, J=9 Hz, 2×Ar$\underline{H}$).

A mixture of the crude (9) (1.13 g, 5 mmol) and (8) (1.42 g, 5 mmol) in THF (30 ml) was stirred for 16 hr at room temperature. The resultant precipitate was filtered to give (10) (1.509 g, 49.0%, from (6)) as a powder.

NMR δ(CDCl$_3$): 2.90–3.60 [5H, m, PMBS—C$\underline{H}$(C$\underline{H}_2$—)$_2$]; 3.73 (3H, s, ArO$\underline{Me}$); 3.77 (2H, s, —C$\underline{H}_2$PhOMe); 5.10 (2H, s, —C$\underline{H}_2$PhNO$_2$); 6.85 (2H, d, J=9 Hz, 2×Ar$\underline{H}$); 7.24 (2H, d, J=9 Hz, 2×Ar$\underline{H}$); 7.55 (2H, d, J=9 Hz, 2×Ar$\underline{H}$); 8.20 (2H, d, J=9 Hz, 2×Ar$\underline{H}$); 8.45 (2H, br, 2×—N$\underline{H}$—).

I.
2-(2-p-Nitrobenzyloxycarbonylimino-hexahydropyrimidine-5-yl)thio-2-methylnitropropane (13)

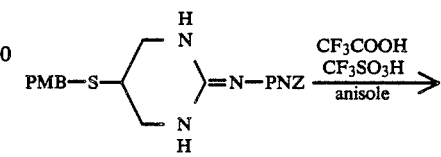

(10)

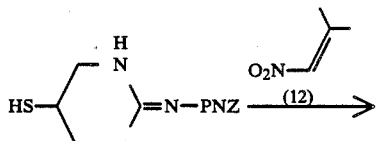

(11)

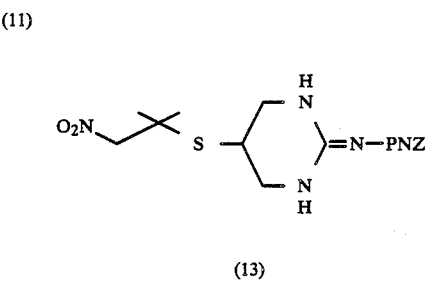

(13)

To a stirred mixture of (10) (620 mg, 1.44 mmol), anisole (1.0 ml) and CF$_3$CO$_2$H were added three drops of CF$_3$SO$_3$H at room temperature, and then stirring was continued for 30 min. After removal of CF$_3$CO$_2$H and CF$_3$SO$_3$H under reduced pressure, the residue and (12) (131 mg, 1.44 mmol) were dissolved in THF (30 ml). To the solution was added Et$_3$N (152 mg, 1.50 mmol) at room temperature, and the mixture was stirred for 30 min. After concentration of the reaction mixture, the residue was purified by column chromatography using CHCl$_3$—MeOH (99:1) to afford (13) (413 mg, 69.7%) as a powder.

NMR δ(CDCl$_3$): 1.40 (6H, s, 2×$\underline{Me}$); 4.74 (2H, s, —C$\underline{H}_2$—NO$_2$); 5.07 (2H, s, —C$\underline{H}_2$Ar); 7.52 (2H, d, J=9 Hz, 2×Ar$\underline{H}$); 8.18 (2H, d, J=9 Hz, 2×Ar$\underline{H}$).

J. 2-[(2-p-Nitrobenzyloxycarbonyliminohexahydropyrimidin-5-yl)-thio]-6-(1-hydroxyethyl)-1-carbadethiapen-2-em-3-carboxylic acid p-nitrobenzylester (15)

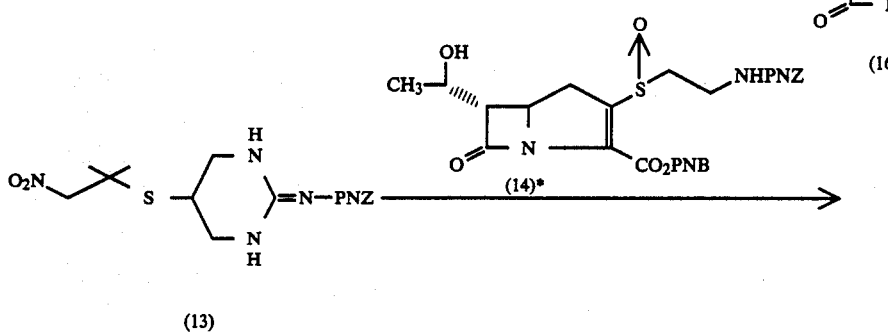

(13)

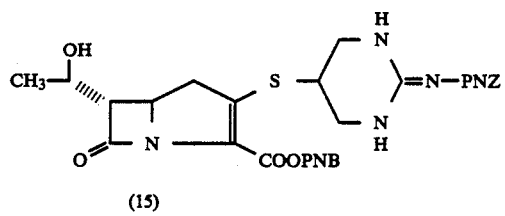

(15)

*N-(p-nitrobenzyloxycarbonyl)-thienamycin sulfoxide p-nitrobenzyl ester)

To a stirred solution of (14) (330 mg, 0.547 mmol) and (13) (360 mg, 0.876 mmol) in THF (5 ml), MeCN (3 ml) and DMSO (3 ml) was added a solution of DBU (117 mg, 0.766 mmol) in THF (1 ml) at −30°. After stirring for 30 min, the reaction mixture was diluted with AcOEt (50 ml), neutralized with 0.5N HCl, washed with water and brine, and dried over MgSO$_4$. After concentration of the reaction mixture, the residue was chromatographed on silica gel using CHCl$_3$—MeOH (9:1) to afford (15) (152 mg, 43.2%) as a powder.

IR υ(KBr): 1770, 1700, 1640, 1610 cm$^{-1}$.

NMR δ(CDCl$_3$—DMSO—d$_6$): 1.29 (3H, d, J=6 Hz, Me); 4.08–4.24 (1H, m, 8—H); 4.24–4.40 (1H, m, 6—H); 5.28 (2H, d, J=14 Hz, ½×—CH$_2$Ar); 5.28 (2H, s, —CH$_2$Ar); 5.54 (2H, d, J=14 Hz, ½—CH$_2$Ar);
  7.61 (2H, d, J=9 Hz, 2×ArH);
  7.72 (2H, d, J=9 Hz, 2×ArH);
  8.23 (2H, d, J=9 Hz, 2×ArH);
  8.24 (2H, d, J=9 Hz, 2×ArH).

K. 2-[(2-Amino-3,4,5,6-tetrahydropyrimidin-5-yl)thio]-6-(1-hydroxyethyl)-1-carbadethiapen-2-em-3-carboxylic acid (16)

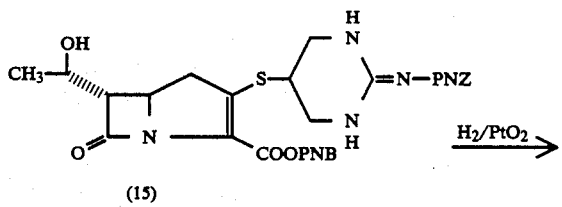

(15)

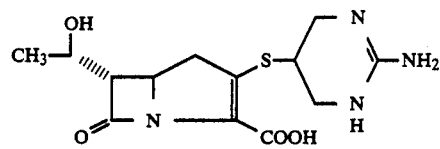

(16)

A mixture of (15)(145 mg, 0.23 mmol), PtO$_2$ (145 mg), THF (11 ml), water (6 ml), EtOH (2 ml) and 1M K$_2$HPO$_4$ (0.33 ml) was submitted to catalytic hydrogenation under 4.2 atm. for 1.5 hr at room temperature. The catalyst was filtered off and washed with water. After concentration of the combined filtrates and washings to remove organic solvents, the aqueous layer was washed with Et$_2$O (20 ml×3). The separated aqueous layer was concentrated to ca. 20 ml. The solution was applied to Diaion HP-20 column chromatography (15×200 m) eluted with water followed by 5% THF. The fractions collected under UV monitoring were liophilized to give a powder, which was further purified by HPLC to afford (16) (7.4 mg, 10.0%) as a powder.

IR υ(KBr): 1760, 1670, 1630, 1570, 1390 cm$^{-1}$.

UV λmax (H$_2$O): 297 nm.

NMR δ(D$_2$O): 1.30 (3H, d, J=6 Hz, Me); 3.05–3.54 (5H, m); 3.60–3.90 (3H, m); 4.20–4.36 (2H, m, C$_5$—H, C$_8$—H).

HPLC column: μ-Bondapak C$_{18}$ 7.8×300 mm; solvent: H$_2$O: MeCN=9:1; flow rate: 3 ml/min; retention time: 5.2 min.

The above compound may also be named as follows: [5R-[5α,6β(R*)]]-3-[(2-amino-1,4,5,6-tetrahydro-5-pyrimidinyl)thio]-6-(1-hydroxyethyl)-7-oxo-1-azabicyclo[3.2.0]hept-2-enecarboxylic acid The synthesis of compound 16 is thus accomplished as follows: The amino groups of compound 1 are protected by exposure to BOC-ON (2-(t-butyloxycarbonyloxyimino)-2-phenylacetonitrile) or di-t-butyl dicarbonate affording compound 2. Conversion of alcohol 2 to tosylate 3 is effected by treatment with tosyl chloride and DMAP (4-dimethylaminopyridine). Introduction of the sulfur atom is accomplished by displacement of the tosylate function of 3 with thiolbenzoic acid and DBU (1,8-diazabicyclo-[5.4.0]undecene) affording thioester 4. Exchange of sulfur protecting groups is accomplished by exposure of 4 to lithiumborohydride yielding free mercaptan 5, followed by alkylation with p-methoxybenzyl chloride and DBU affording thioether 6. The required thiocarbamate reagent 7 is prepared by the reaction of p-nitrobenzyl chloroformate with potassium thiocyanate, followed by a methanol quench. S-alkylation of 7 with dimethyl sulfate provides guanidine precursor 8. Construction of the guanidine is accomplished by exposure of 6 to trifluoroacetic acid affording free diamine 9, followed by treatment with thioimidate 8 to yield protected guanidine 10. Exchange of S-protecting groups is effected by exposure of 10 to a mixture of trifluoroacetic acid, trifluoromethanesulfonic acid and anisole to yield free thiol 11, followed by treatment with 1-nitro-2-methylpropene and triethylamine affording 13. Exposure of protected thienamycin sulfoxide 14 to 13 and DBU provides the protected carbapenem derivative 15. Removal of the protecting groups is achieved by hydrogenolysis over platinum oxide to yield free carbapenem 16.

EXAMPLE 2

A.
1-Chloro-2-(N-methyl-N-t-butoxycarbonylamino)-1-cyanoethane (19)

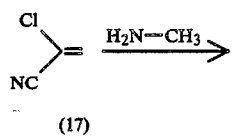

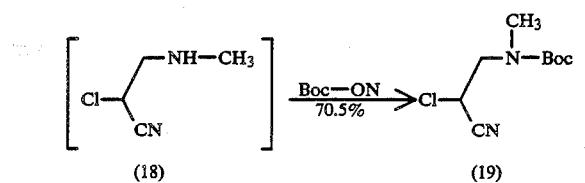

To a stirred solution of (17) (5 g, 57 mmol) in dioxane (100 ml) was added 40% aqueous methylamine (4.3 ml, 55 mmol) at room temperature. After stirring for 6 hr, Boc—ON (14 g, 57 mmol) was added to the reaction mixture and stirring was continued for additional 72 hr at room temperature. Removal of the solvent gave a residue, which was chromatographed on silica gel using benzene to afford (19) (8.8 g, 70.5%) as an oil.

NMR δ (CDCl$_3$): 1.50 (9H, s, —C(Me)$_3$)
3.06 (3H, s, —NMe)
3.65–3.75 (2H, m, —CH$_2$—)

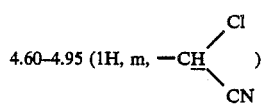
4.60–4.95 (1H, m, —CH(Cl)(CN))

B.
2-(N-t-Butoxycarbonyl-N-methylamino)-1-cyano-1-p-methoxybenzylthioethane (20)

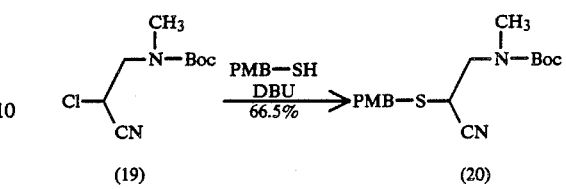

To a stirred mixture of (19), (9.14 g, 41.8 mmol) and PMB—SH (6.45 g, 41.8 mmol) in benzene (100 ml) was added DBU (10.7 g, 70.3 mmol), and stirring was continued for 3 hr. The reaction mixture was washed with water and brine, dried over MgSO$_4$ and concentrated. The residue was purified by silica gel column chromatography using benzene to give (20) (9.34 g, 66.5%) as an oil.

NMR δ(CDCl$_3$): 1.40 (9H, s, —C(Me)$_3$); 2.90 (3H, s, —N(Me)—Boc); 3.20–3.90 (3H, m, —CH$_2$—CH(CN)—SPMB); 3.78 (3H, s, ArOMe); 3.90 (2H, s, —CH$_2$Ar); 6.83 (2H, d, J=9 Hz, 2×ArH); 7.25 (2H, d, J=9 Hz, 2×ArH).

C.
1-Amino-3-(N-t-butoxycarbonyl-N-methylamino)-2-p-methoxybenzylthiopropane (21)

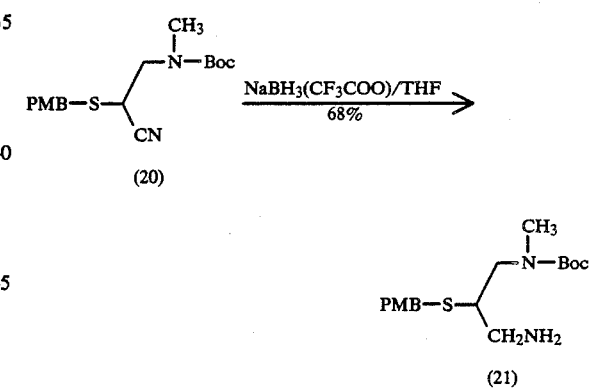

To an ice-cold suspension of NaBH$_4$ (2.25 g, 59.5 mmol) in THF (100 ml) was slowly added CF$_3$CO$_2$H (6.60 g, 59.5 mmol) with stirring. To the resulting mixture was added a solution of (20) (4 g, 11.9 mmol) in THF (20 ml) at room temperature, and stirring was continued for 4 hr. Excess NaBH$_4$ was quenched by adding water, and the mixture was concentrated. The residue was extracted with CHCl$_3$ (180 ml×3). The combined extracts were washed with brine and dried over MgSO$_4$. Removal of the solvent gave a residue, which was chromatographed on silica gel using 3% MeOH—CHCl$_3$ to afford (21) (2.77 g, 68.0%) as an oil.

NMR δ(CDCl$_3$): 1.45 (9H, s, —C(Me)$_3$); 2.60–3.15 (4H, m, H$_2$N—CH$_2$—CH—CH$_2$—N(Me)—Boc); 3.72 (2H, s, —CH$_2$Ar); 3.80 (3H, s, ArOMe); 6.85 (2H, d, J=9 Hz, 2×ArH); 7.24 (2H, d, J=9 Hz, 2×ArH).

D.
1-Amino-2-p-methoxybenzylthio-3-(N-methylamino)-propane (22)

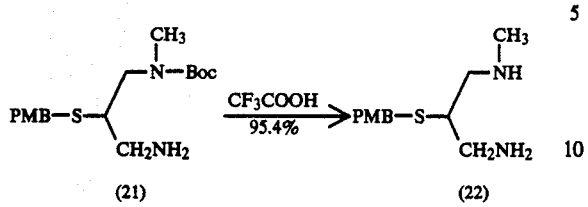

To an ice-cold mixture of (21) (3.0 g, 12.5 mmol) and anisole (5 ml) was added CF$_3$CO$_2$H (30 ml) with stirring, and stirring was continued for 30 min under ice-cooling and additional 30 min at room temperature. After removal of CF$_3$CO$_2$H under reduced pressure, the oily residue was partitioned between water (100 ml) and benzene (100 ml). The separated aqueous layer was made alkaline with conc. NH$_4$OH, and extracted with CHCl$_3$ (200 ml×3). The organic layer was dried over MgSO$_4$ and concentrated to give (22) (2.02 g, 95.4%) as a crude oil.

NMR δ(CDCl$_3$): 1.34 (3H, s, —NHMe, —NH$_2$); 2.38 (3H, s, —NHMe); 2.50–3.05 (5H, m, MeHN—CH$_2$—CH—CH$_2$—NH$_2$); 3.71 (2H, s, —CH$_2$Ar); 3.80 (3H, s, —ArOMe); 6.83 (2H, s, 2×ArH); 7.25 (2H, s, 2×ArH).

E.
2-Amino-5-p-methoxybenzylthio-1-methyl-1,4,5,6-tetrahydropyrimidine hydrochloride (23)

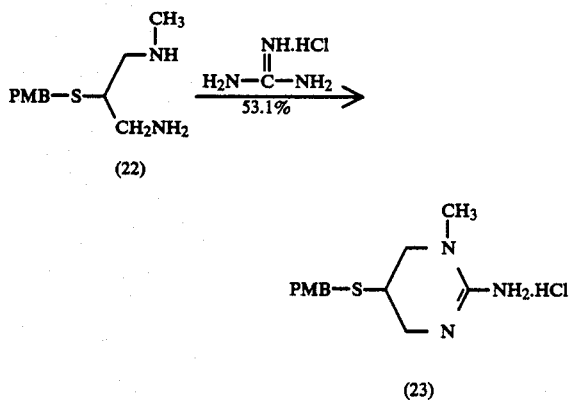

A mixture of (22) (1.5 g, 6.25 mmol) and guanidine hydrochloride (597 mg, 6.25 mmol) was heated at 140° for 4 hr. The reaction mixture was purified by silica gel column chromatography using CHCl$_3$—MeOH (19:1) to give (23) (1.0 g, 53.1%) as a powder. NMR δ(CDCl$_3$): 3.09 (3H, s, —NMe—); 2.80–3.80 (5H, m, —S—CH(CH$_2$—)$_2$); 3.78 (5H, s, —CH$_2$—Ar—OMe); 6.83 (2H, d, J=9 Hz, 2×ArH); 7.21 (2H, d, J=9 Hz, 2×ArH).

F.
2-Amino-5-mercapto-1-methyl-1,4,5,6-tetrahydropyrimidine trifluoromethanesulfonate (24)

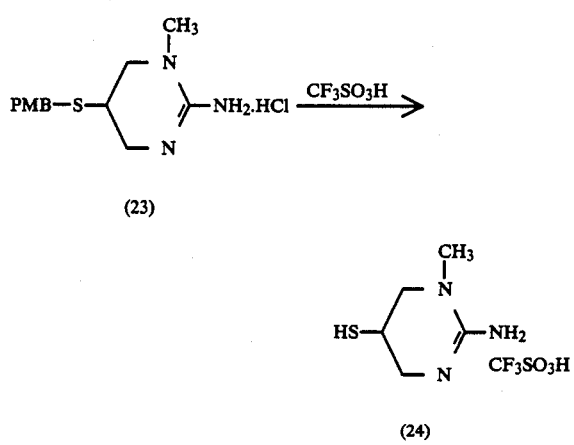

To a stirred mixture of (23) (1.0 g, 33.2 mmol), anisole (3ml) and CF$_3$CO$_2$H (10 ml) was added CF$_3$SO$_3$H (0.5 ml), and stirring was continued for 1 hr. After removal of CF$_3$CO$_2$H under reduced pressure, the residue was washed with n-pentane to give (24) (896 mg, 91.6%) as an oil.

NMR δ(CDCl$_3$): 3.00 (3H, s, —NMe—); 3.00–3.80 (m).

G.
2-[(2-Amino-1-methyl-1,4,5,6-tetrahydropyrimidine-5-yl)thio]-6-(1-hydroxyethyl)-1-carbadethiapen-2-em-3-carboxylic acid (25A and 25B)

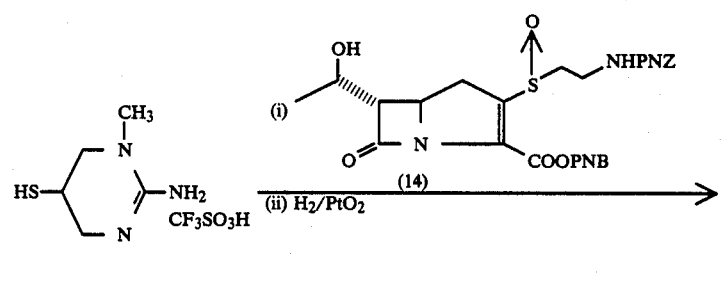

-continued

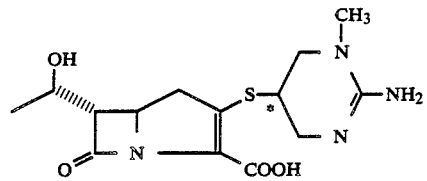

(25A) (isomer A) 2.1%
(25B) (isomer B) 3.3%

To a stirred solution of (14) (301 mg, 0.5 mmol), and (24) (295 mg, 1 mmol) in DMF* (5 ml) was added a solution of i—Pr$_2$NEt (129 mg, 1 mmol) at −40° under argon. After stirring for ¼ hr at the same temperature, the mixture was poured into ether (40 ml) and centrifuged to give a gummy precipitate. A mixture of the precipitate, THF (15 ml), water (15 ml), 0.1M phosphate buffer (pH 6.0, 15 ml) and PtO$_2$ (150 mg) was submitted to catalytic hydrogenation under 4 atm. for 1 hr at room temperature. The catalyst was removed by filtration and washed with water. The filtrate and washings were combined, and concentrated under reduced pressure to remove organic solvents. The resultant aqueous solution was washed with AcOEt (30 ml×2), then concentrated to ca. 30 ml. The residue was applied to Diaion-HP20 column chromatography (15×230 mm) using water and 5% THF with continuous UV monitoring. The fraction eluted with 5% THF was concentrated, and then purified by HPLC to give (25A) (3.5 mg, 2.1%) and (25B) (5.6 mg, 3.3%) as a powder.
*Dimethylformamide (25A)
UV λmax (H$_2$O): 296 nm;
IR υ(KBr): 1755 cm$^{-1}$.
NMR δ(D$_2$O): 1.24–1.36 (3H, m, —CH(OH)Me); 3.02 (3H, m, —NMe—); 3.10–4.00 (8H, m); 4.10–4.40 (2H, m, C$_5$—H and C$_8$—H).

(25B)
UV λmax (H$_2$O): 296 nm.
IR υ(KBr): 1755 cm$^{-1}$.
NMR δ(D$_2$O): 1.24–1.36 (3H, m); 3.04 (3H, s, —NMe—); 3.10–3.90 (8H, m); 4.10–4.35 (2H, m, C$_5$—H and C$_8$—H).

HPLC column: μ-Bondapak C$_{18}$ 7.8 mm×30 cm; solvent: MeCN—H$_2$O (1:19); flow rate: 3.0 ml/min; retention time: (25A) 7.3 min, (25B) 8.0 min.

Substituted guanidine derivatives such as 25 may thus be prepared as follows: Exposure of α-chloroacrylonitrile to a primary alkylamine followed by protection with BOC—ON affords carbamate 19. Introduction of sulfur is accomplished by treatment of 19 with p-methoxybenzyl mercaptan and DBU to yield thioether 20. Reduction of the nitrile function in 20 with sodium-borohydride and trifluoroacetic acid affords amine 21, which is deprotected by exposure to trifluoroacetic acid to yield diamine 22. Trans-guanidinylation is effected by heating 22 with guanidine hydrochloride affording 23. S-deprotection occurs upon exposure of 23 to a mixture of trifluoroacetic acid, trifluoromethanesulfonic acid and anisole to yield mercapto guanidine salt 24. Treatment of protected thienamycin sulfoxide 14 with 24 and diisopropyl ethylamine, followed by hydrogenolysis over platinum oxide affords carbapenem antibiotics 25.

EXAMPLE 3

A. 2-p-Methoxybenzylthio-5-phthalimidoylpentanoic acid (27)

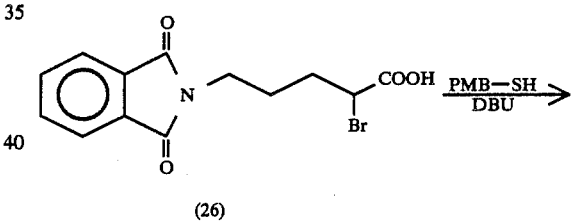

(26)

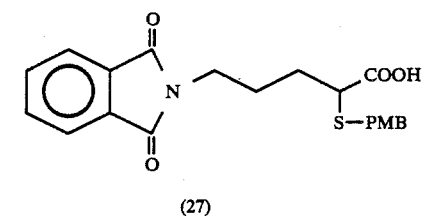

(27)

To a solution of (26)* (10.5 g, 32.2 mmol) and PMB.SH (5.8 g, 37.6 mmol) in DMF (35 ml) was added DBU (10.7 g, 70.3 mmol), and stirring was continued for 20 min at room temperature. The mixture was poured into cold 10% HCl and extracted with AcOEt. The extract was washed repeatedly with H$_2$O and dried over MgSO$_4$. Removal of the solvent gave a residue which was chromatographed on silica gel (100 g) using CHCl$_3$—MeOH (50:1 v/v) as an eluent to give (27) (13.1 g, quant.) as a pale yellow viscous oil.
*R. Gaudry and L. Berlinguet, Can. J. Research, 28B, 245 (1950).

NMR δ(CDCl$_3$): 1.5–2.0 (4H, m, —C$_3$—H$_2$, —C$_4$H$_2$); 3.0–3.3 (1H, m, —C$_2$—H); 3.4–3.8 (2H, m, —C$_5$—H$_2$); 3.77 (3H, s, —OCH$_3$); 3.80 (2H, s, ArCH$_2$—); 6.80 (2H, d, J=9 Hz, ArH×2); 7.21 (2H, d, J=9 Hz, ArH×2); 7.6–7.9 (4H, m ArH×4); 8.3–8.9 (1H, m —COOH).

B. 5-t-Butoxycarbonylamino-2-p-methoxybenzylthiopentanoic acid (28)

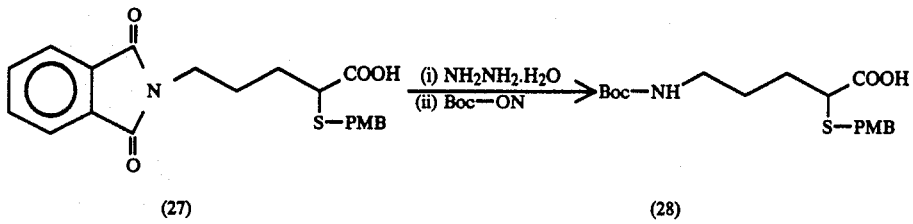

To a solution of (27) (4.6 g, 11.5 mmol) in EtOH (50 ml) was added H₂NNH₂.H₂O (3 ml) at room temperature and stirring was continued for 17 hr. After concentration of the reaction mixture under reduced pressure, 5% HCl (100 ml) was added to the residue, then the mixture was centrifuged. The supernatant was concentrated under reduced presure and the residue was dissolved in dioxane (50 ml) and H₂O (50 ml). Boc—ON (8.5 g, 34.6 mmol) and Et₃N (4.6 g, 46 mmol) were added to the solution at room temperature and stirring was continued for 3 hr. The reaction mixture was washed with Et₂O, and the aqueous layer was acidified with HCl and extracted with AcOEt. The extract was washed with brine, dried over Na₂SO₄ and concentrated under reduced pressure. The residue was chromatographed on silica gel (75 g) using CHCl₃—MeOH (99:1 v/v) as an eluent to give (28) (3.4 g, 80%).

NMR δ(CDCl₃): 1.44 (9H, s, Boc—methyl); 1.40–1.95 (4H, m); 2.90–3.30 (3H, m); 3.78 (5H, br s, OCH₃ and SCH₂Ar); 6.81 and 7.24 (each 2H, each d, J=9 Hz, 4×ArH); 9.33 (1H, br s, CO₂H).

C. 5-t-Butoxycarbonylamino-2-p-methoxybenzylthiopentamide (29)

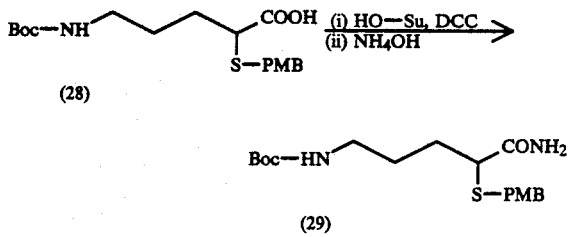

To a stirred solution of (28) (3.4 g, 9.2 mmol) in THF (30 ml) were added N-hydroxysuccinimide (1.06 g, 9.2 mmol) and DCC* (1.9 g, 9.2 mmol) at room temperature. After stirring for 30 min, conc. NH₄OH (24 ml) was added to the reaction mixture and stirring was continued for additinal 17 hr. The reaction mixture was filtered and the filtrate was diluted with AcOEt. The organic layer was washed with H₂O and brine, dried over Na₂SO₄, then concentrated. The residue was chromatographed on silica gel (50 g) using CHCl₃—MeOH (99:1 v/v) as an eluent to give (29) (2 g, 59%).

*dicyclohexylcarbodiimide

NMR δ(CDCl₃): 1.43 (9H, s, Boc—methyl); 1.40–2.00 (4H, m); 2.90–3.30 (3H, m); 3.70 (2H, s, SCH₂Ar); 3.76 (3H, s, OCH₃); 4.79 (1H, br, NH); 6.23 and 6.51 (each 1H, each br s, NH₂); 6.81 and 7.18 (each 2H, each d, J=9 Hz, 4×ArH).

D. 5-Butoxycarbonylamino-2-p-methoxybenzylthiopentanonitrile (30)

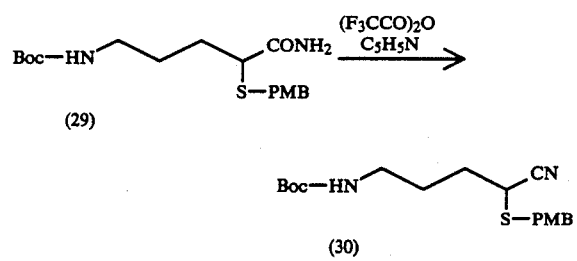

To a stirred solution of (29) (1.89 g, 5.14 mmol) in dioxane (14 ml) and pyridine (811 mg, 10.3 mmol) was added dropwise (CF₃CO)₂O (1.08 g, 5.14 mmol) at 0°–5° C. After stirring for 1 hr at room temperature, the reaction mixture was diluted with AcOEt, washed with H₂O, dried over Na₂SO₄ and concentrated. The residue was chromatographed on silica gel (35 g) using CHCl₃ as an eluent to give (30) quantitatively.

NMR δ(CDCl₃): 1.42 (9H, s, Boc—methyl); 1.50–1.90 (4H, m); 2.95–3.20 (2H, m); 3.23–3.45 (1H, m); 3.76 (3H, s, OCH₃); 3.87 (2H, s, SCH₂Ar); 4.65–4.86 (1H, m, NH); 6.81 and 7.21 (each 2H, each d, J=9 Hz, 4×ArH).

E. 5-Amino-2-p-methoxybenzylthiopentanonitrile (31)

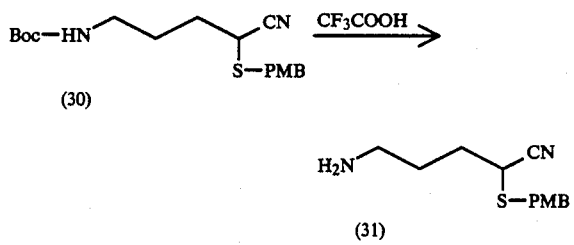

A mixture of (30) (700 mg, 2 mmol), anisole (1.4 ml, 12.6 mmol) and CF₃CO₂H (8 ml) was stirred for 1 hr at 0°–5°, and the reaction mixture was concentrated under reduced pressure. The residue was washed with petroleum ether and dissolved in CHCl₃. The solution was washed with NaHCO₃, H₂O and brine, dried over Na₂SO₄, then concentrated to give (31) (480 mg, 96%).

NMR δ(CDCl₃): 1.40–2.00 (4H, m); 2.61 (2H, t, J=6 Hz, CH₂NH₂); 3.32 (1H, t, J=6 Hz, CH); 3.73 (3H, s, OCH₃); 3.85 (2H, s, SCH₂Ar); 6.81 and 7.22 (each 2H, each d, J=9 Hz, 4×ArH).

F. 2-Imino-3-p-methoxybenzylthiopiperidine Tosylate (32)

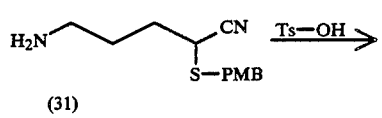

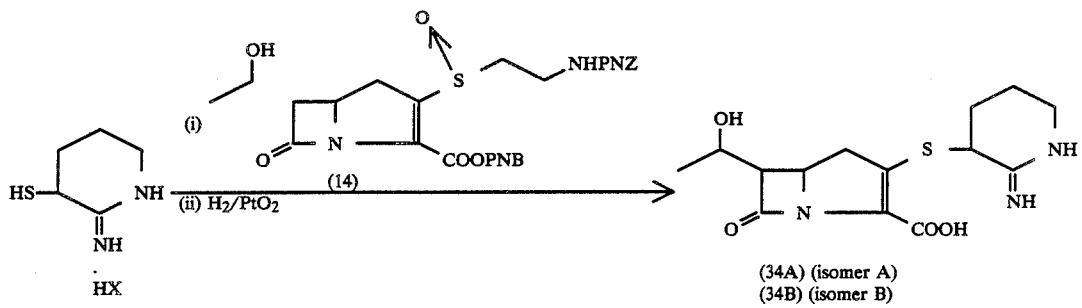

A mixture of (31) (480 mg, 1.92 mmol) and TsOH.-H$_2$O (380 mg, 2 mmol) in xylene (10 ml) was heated under reflux for 48 hr. After removal of the solvent, the residue was chromatographed on silica gel (10 g) using CHCl$_3$—MeOH (98:2 v/v) to give (32) (430 mg, 53%), which was triturated with Et$_2$O to give a yellowish powder.

NMR δ(CDCl$_3$): 1.60–2.10 (4H, m); 2.34 (3H, s, CH$_3$); 3.25–3.46 (2H, m); 3.76 (3H, s, OCH$_3$); 3.83 and 4.00 (each 1H, each d, J=14 Hz, SCH$_2$Ar); 6.76 (2H, d, J=9 Hz, 2×ArH); 7.10–7.30 (4H, m $\overline{4\times}$ArH); 7.75 (2H, d, J=9 Hz, 2×ArH); 7.90, 9.10 and 9.85 (each 1H, each br s).

G. 2-Imino-3-mercaptopiperidine Tosylate (33)

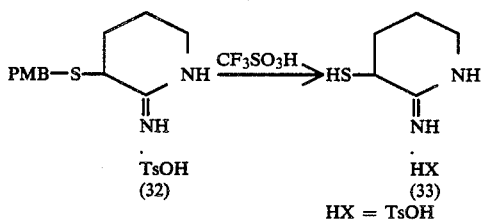

To a mixture of (32) (430 mg, 1.02 mmol) and anisole (0.7 ml) in CF$_3$CO$_2$H (4 ml) was added CF$_3$SO$_3$H (10 drops) at room temperature and stirring was contnued for 30 min. The reaction mixture was concentrated under reduced pressure and the residue was washed with petroleum ether to give (33) quantitatively as an oil.

NMR δ(D$_2$O): 1.70–2.20 (4H, m); 2.20 (3H, s, CH$_3$); 3.30–3.60 (2H, m); 3.83–4.03 (1H, m); 4.80 (HOD); 7.36 and 7.70 (each 2H, each d, J=9 Hz, 4×ArH).

H. 6-(1-Hydroxyethyl)-2-(2-iminopiperidin-3-yl)thio-1-carbadethiapen-2-em-3-carboxylic acid (34A, 34B)

To a stirred solution of (14) (210 mg, 0.35 mmol) in DMF (4 ml) were added (33) (160 mg, 0.56 mmol) in DMF (1 ml) and DBU (82 mg) at −40° under argon. After stirring for 40 min, the reaction mixture was diluted with THF (17 ml), H$_2$O (8 ml), and 1/15M phosphate buffer (pH 6) (17 ml). PtO$_2$ (210 mg) was added to this solution and the whole was subjected to catalytic hydrogenation under 4 atm. for 45 min at room temperature, then cooled below 5°. The catalyst was removed by filtration and washed with H$_2$O. The filtrate and washings were combined, washed with CHCl$_3$ and concentrated to ca. 30 ml under reduced pressure. The solution was applied to Diaion-HP20 column chromatography (20×250 mm) using H$_2$O and 5% THF respectively as eluents. The fraction eluted with 5% THF was found to contain 1-carbapenem derivative by UV assay, and further purified by HPLC to give (34A) (4 mg) and (34B) (4 mg).

(34A)
UV λ(H$_2$O): 297 nm.
IR ν(KBr): 1760, 1680, 1590 cm$^{-1}$.
NMR δ(D$_2$O): 1.28 (3H, d, J=6 Hz, CH$_3$); 1.70–2.32 (4H, m); 3.19–3.30 (2H, m); 3.40–3.60 (3H, m); 4.20–4.36 (3H, m); 4.80 (HOD).

(34B)
IR ν(KBr): 1760, 1680, 1580 cm$^{-1}$.
NMR δ(D$_2$O): 1.27 (3H, d, J=6 Hz, CH$_3$); 1.80–2.16 (3H, m); 2.20–2.36 (1H, m); 3.12–3.28 (2H, m); 3.40–3.60 (3H, m); 4.10–4.32 (3H, m); 4.80 (HOD).

In the additional experiment, (34B) was obtained as needles from water.

Anal. calcd for C$_{14}$H$_{19}$N$_3$O$_4$S.2H$_2$O: C, 46.53; H, 6.41; N, 11.63. Found: C, 46.88; H, 5.88; N, 11.09.

UV λ(H$_2$O): 297 nm (Σ 10400) [α]$_D^{25}$= +40.0° (H$_2$O, C=0.19) (corrected value for the unhydrate).

HPLC: column: μ-Bondapak C$_{18}$(7.8×300 mm); solvent: MeCN-H$_2$O=5:95 v/v; flow rate: 3 ml/min; retention time: (34A): 11 min, (34B): 12 min.

The above two isomers may also be named as follows:

[5R—[3(R*),5α,6β(R*)]]-3-[(2-amino-3,4,5,6-tetrahydro-3-pyridinyl)thio]-6-(1-hydroxyethyl)-7-oxo-]-azabicyclo[3.2.0]hept-2-enecarboxylic acid.

[5R-[3(S*),5α,6β(R*)]]-3-[(2-amino-3,4,5,6-tetrahydro-3-pyridinyl)thio]-6-(1-hydroxyethyl)-7-oxo-]-azabicyclo[3.2.0]hept-2-enecarboxylic acid.

Cyclic amidines such as 34 are thus prepared as follows: Treatment of the known bromo acid 26 with p-methoxybenzylmercaptan and DBU affords thioether 27. Exchange of the amine protecting groups is accomplished by removal of the phthalimidyl group with hydrazine followed by reprotection with BOC-ON to yield 28. Conversion of acid 28 to primary amide 29 is effected by activation with N-hydroxysuccinimide and dicyclohexyl carbodiimide followed by an ammonia quench. Exposure of 29 to trifluoroacetic anhydride and pyridine affords nitrile 30, which is N-deprotected by treatment with trifluoroacetic acid and anisole to yield aminonitrile 31. Cyclization to the amidine salt 32 is effected by heating 31 with an equivalent amount of p-toluenesulfonic acid. Exposure of 32 to trifluoroacetic acid, trifluoromethanesulfonic acid and anisole effects S-deprotection affording thiol 33. Treatment of carbapenem sulfoxide 14 with 33 and DBU, followed by hydrogenolysis over platinum oxide affords amidinyl carbapenems 34.

EXAMPLE 4

A. 3-t-Butoxycarbonylaminopropanol (36)

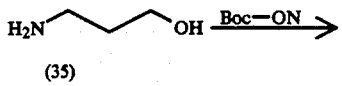

(35)

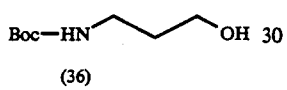

(36)

A mixture of (35) (1.5 g, 20 mmol) and Boc—ON (5.8 g, 24 mmol) in dioxane (30 ml) was stirred for 2 hr at room temperature. The reaction mixture was concentrated, and the residue was chromatographed on silica gel (80 g) using benzene—AcOEt (9:1 v/v) as an eluent to give (36) quantitatively.

NMR δ(CDCl$_3$): 1.44 (9H, s, Boc—methyl); 1.66 (2H, quint, J=6 Hz, CH$_2$CH$_2$OH); 3.26 (2H, q, J=6 Hz, NHCH$_2$—); 3.64 (2H, t, J=6 Hz, CH$_2$OH); 4.86 (1H, br, NH).

B. 3-(N-Methyl-N-t-butoxycarbonyl)aminopropanol (37)

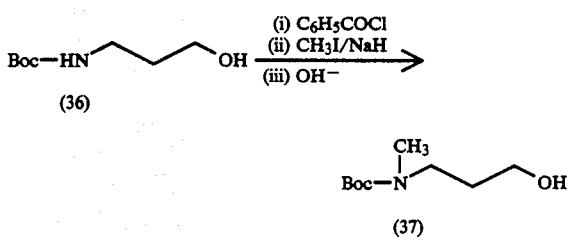

To a solution of (36) (2.16 g, 12.3 mmol) and Et$_3$N (1.48 g, 14.8 mmol) in THF (15 ml) was added dropwise PhCOCl (1.73 g, 12.3 mmol) at 0°-5° with stirring. After stirring for additional 17 hr at room temperature, the resulting precipitate was filtered off. The filtrate was concentrated under reduced pressure, and the residue was dissolved in DMF (5 ml). MeI (3.5 g, 24.6 mmol) and 60% NaH (600 mg, 15 mmol) were added to the solution and stirring was continued for 2 hr at room temperature. To the reaction mixture were added H$_2$O and 2.5N NaOH with stirring. After stirring for 10 min, AcOEt was added to the reaction mixture. The separated organic layer was washed with H$_2$O and brine, dried over Na$_2$SO$_4$, then concentrated. The residue was chromatographed on silica gel (20 g) using benzene-AcOEt (9:1 v/v) as an eluent to give (37) (1.2 g, 50%).

NMR δ(CDCl$_3$): 1.45 (9H, s, Boc—methyl); 1.69 (2H, quint, J=6 Hz, —CH$_2$CH$_2$OH); 2.83 (3H, s, NCH$_3$); 3.35 (2H, t, J=6 Hz, NCH$_2$—); 3.55 (2H, m, —CH$_2$OH).

C. 3-(N-Methyl-N-t-butoxycarbonyl)aminopropyl Tosylate (38)

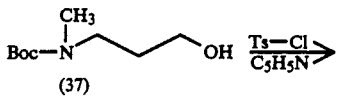

(37)

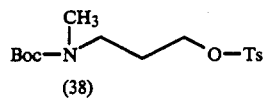

(38)

A mixture of (37) (1.75 g, 9.26 mmol) and TsCl (2.65 g, 14 mmol) in pyridine (20 ml) was stirred for 17 hr at 0°-5°. The reaction mixture was diluted with AcOEt, washed with H$_2$O, dried over Na$_2$SO$_4$ and concentrated. The residual oil was chromatographed on silica gel (40 g) using benzene—AcOEt (95:5 v/v) as an eluent to give (38) (1.63 g, 51.4%).

NMR δ(CDCl$_3$): 1.43 (9H, s, Boc—methyl); 1.86 (2H, quint, J=6 Hz, —CH$_2$CH$_2$CH$_2$—); 2.44 (3H, s, CH$_3$); 2.79 (3H, s, NCH$_3$); 3.24 (2H, t, J=6 Hz, NCH$_2$); 4.03 (2H, t, J=6 Hz, —CH$_2$OTs); 7.31 and 7.75 (each 2H, each d, J=9 Hz, 4×ArH).

D. 3-(N-t-Butoxycarbonyl-N-methyl)aminopropyl Iodide (39)

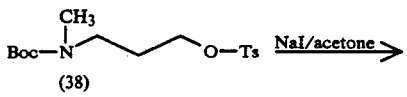

(38)

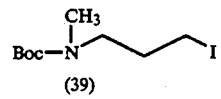

(39)

To a solution of (38) (450 mg, 1.31 mmol) in acetone (13 ml) was added NaI (1.97 g, 13.1 mmol) at room temperature with stirring. After stirring for 17 hr, the solvent was removed. Benzene was added to the residue and the precipitate was filtered off. The filtrate was concentrated and the residue was chromatographed on silica gel (7 g) using benzene as an eluent to give (39) (300 mg, 51%).

NMR δ(CDCl$_3$): 1.46 (9H, s, Boc—methyl); 2.05 (2H, m, —CH$_2$CH$_2$CH$_2$I); 2.86 (3H, s, NCH$_3$); 3.14 and 3.29 (each 2H, each t, J=6 Hz, NCH$_2$CH$_2$CH$_2$I).

E. Ethyl 2-p-methoxybenzylthiocyanoacetate (41)

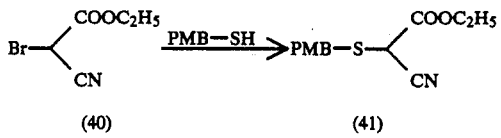

(40)    (41)

To an ice-cold solution of (40) (8.7 g) in CHCl$_3$ (100 ) were successfully added PMB—SH (4.62 g, 0.03 mol)

in CHCl₃ (10 ml) and Et₃N (3.03 g, 0.03 mol) in CHCl₃ (10 ml). The mixture was stirred for 15 min in an ice bath and additional 30 min at room temperature. The reaction mixture was washed with water, dried over Na₂SO₄ and concentrated under reduced pressure to give an oil. A solution of the oil in benzene was washed with 5% aqueous NaHCO₃ solution and extracted with 0.25N NaOH. The separated aqueous layer was acidified with dil. HCl and extracted with CHCl₃. The organic phase was washed with water, dried over Na₂SO₄ and concentrated under reduced pressure to give (41) (1.043 g) as a pale yellow oil.

NMR δ(CDCl₃): 1.28 (3H, t, J=7 Hz, —CH₃); 3.77 (3H, s, OCH₃); 3.96 (2H, s, —S—CH₂—); 4.05 (1H, s, —CH ); 4.18 (2H, q, J=7 Hz, —CH₂—CH₃); 6.81 and 7.23 (each 2H, each d, J=9 Hz, ArH×4).

Mass: m/e 265 (M⁺).

IR υ(neat): 2240 (CN), 1740 (C=O) cm⁻¹.

F.
5-Butoxycarbonyl-N-methyl)amino-2-ethoxycarbonyl-2-p-methoxybenzylthiopentanonitrile (42)

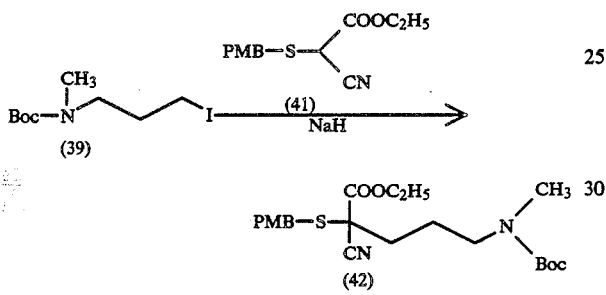

To a mixture of (39) (179 mg, 0.6 mmol) and (41) (133 mg, 0.5 mmol) in DMF (2 ml) was added 60% NaH (24 mg, 0.6 mmol) at 0°-5° with stirring. After stirring for 17 hr at room temperature, the reaction mixture was diluted with AcOEt. The diluted mixture was washed with H₂O, dried over Na₂SO₄, and concentrated under reduced pressure. The residue was chromatographed on silica gel (6 g) using benzene—AcOEt (98:2 v/v) as an eluent to give (42) (150 mg, 69%).

NMR δ(CDCl₃): 1.28 (3H, t, J=6 Hz, OCH₂CH₃); 1.44 (9H, s, Boc—methyl); 1.50–2.10 (4H, m, NCH₂CH₂CH₂—); 2.81 (3H, s, NCH₃); 3.16–3.38 (2H, m, NCH₂—); 3.76 (3H, s, OCH₃); 4.01 (2H, s, —SCH₂Ar); 4.13 (2H, q, J=6 Hz, OCH₂CH₃); 6.80 and 7.22 (each 2H, each d, J=9 Hz, 4×ArH).

G.
5-(N-t-Butoxycarbonyl-N-methyl)amino-2-p-methoxybenzylthiopentanonitrile (43)

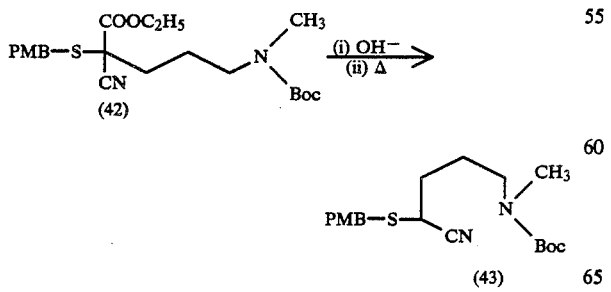

To a solution of (42) (690 mg, 1.59 mmol) in EtOH (6 ml) and H₂O (3 ml) was added 2.5N NaOH (1.6 ml) at 0°-5° with stirring. After stirring for 20 min, the reaction mixture was diluted with AcOEt and acidified with HCl. The separated organic layer was dried over Na₂SO₄ and concentrated. The residue was heated at 120° for 10 min and the reaction mixture was chromatographed on silica gel (6 g) using CHCl₃ as an eluent to give (43) (510 mg, 88.4%).

NMR δ(CDCl₃): 1.42 (9H, s, Boc—methyl); 1.60–1.85 (4H, m); 2.78 (3H, s, NCH₃); 3.10–3.45 (3H, m); 3.76 (3H, s, OCH₃); 3.87 (2H, s, SCH₂Ar); 6.82 and 7.22 (each 2H, each d, J=9 Hz, 4×ArH).

H.
5-Methylamino-2-p-methoxybenzylthiopentanonitrile (44)

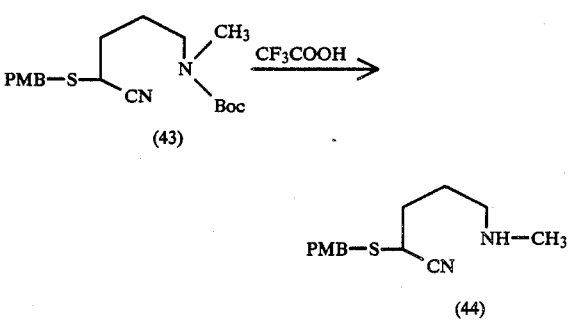

A mixture of (43) (830 mg, 2.29 mmol), anisole (1.7 ml) and CF₃CO₂H (10 ml) was stirred for 30 min at 0°-5° and concentrated under reduced pressure. The residue was washed with petroleum ether and dissolved in CHCl₃. The solution was washed with NaHCO₃, H₂O, and brine, dried over Na₂SO₄, then concentrated to give (44) quantitatively.

NMR δ(CDCl₃): 1.50–2.00 (4H, m); 2.36 (3H, s, NCH₃); 2.52 (2H, t, J=6 Hz, NCH₂—); 3.33 (1H, t, J=6 Hz, CH); 3.76 (3H, s, OCH₃); 3.86 (2H, s SCH₂Ar); 6.81 and 7.22 (each 2H, each d, J=9 Hz, 4×ArH).

I. 2-Imino-3-p-methoxybenzylthio-1-methylpiperidine Tosylate (45)

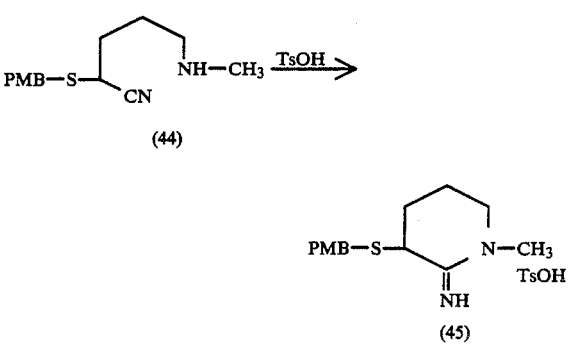

A mixture of (44) (550 mg, 2.08 mmol) and TsOH·H₂O (396 mg, 2.08 mmol) in xylene (10 ml) was heated under reflux for 24 hr. After removal of the solvent, the residue was chromatographed on silica gel (5 g) using CHCl₃—MeOH (98:2 v/v) as an eluent to give (45) (780 mg, 86%), which was triturated with Et₂O to give (45) as a powder.

NMR δ(CDCl₃): 1.60–2.10 (4H, m); 2.30 (3H, s, CH₃); 3.10 (3H, s, NCH₃); 3.15–3.40 (2H, m); 3.73 (3H, s, OCH$_3$); 3.83 and 4.08 (each 1H, each d, J=15 Hz, SCH$_2$Ar); 4.10–4.23 (1H, m); 6.71 (2H, d, J=9 Hz, 2×ArH); 7.00–7.25 (4H, m, 4×ArH); 7.75 (2H, d, J=9 Hz, 2×ArH); 8.89 (2H, br s).

J. 2-Imino-3-mercapto-1-methylpiperidine Tosylate (46)

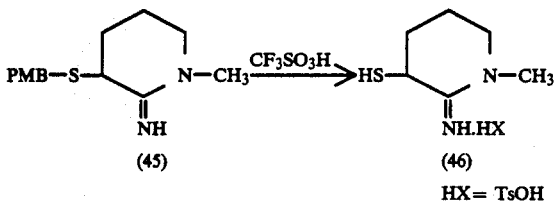

To a mixture of (45) (436 mg, 1 mmol) and anisole (0.7 ml) in CF$_3$CO$_2$H (4 ml) was added CF$_3$SO$_3$H (10 drops) at room temperature and stirring was continued for 30 min. The reaction mixture was concentrated under reduced pressure, and the residue was washed with petroleum ether to give (46) as an oil.

NMR δ(D$_2$O): 1.65–2.35 (4H, m); 2.40 (3H, s, CH$_3$); 3.07 (3H, s, NCH$_3$); 3.40–3.60 (2H, m); 3.88–4.03 (1H, m); 4.80 (HOD); 7.35 and 7.70 (each 2H, each d, J=9 Hz, 4×ArH).

K.
6-(1-Hydroxyethyl)-2-(2-imino-1-methylpiperidin-3-yl)thio-1-carbadethiapen-2-em-3-carboxylic acid (47A and 47B)

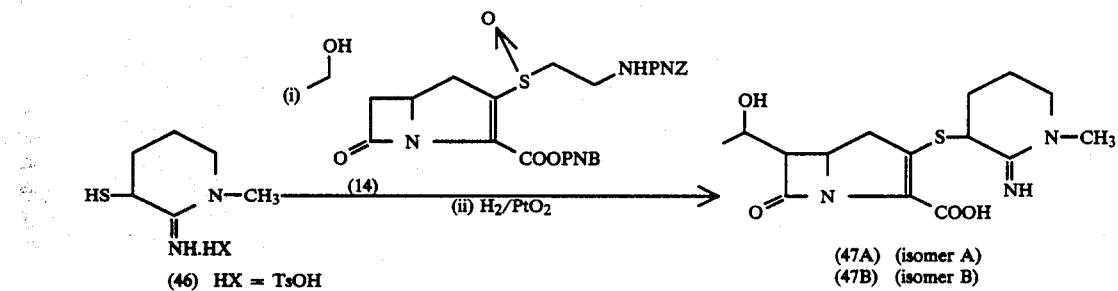

To a stirred solution of (14) (180 mg, 0.3 mmol) in DMF (3 ml) were added (46) (143 mg, 0.45 mmol) in DMF (1 ml) and DBU (70 mg, 0.45 mmol) at −40° under argon. After stirring for 40 min, the reaction mixture was diluted with THF (15 ml), H$_2$O (7 ml) and 1/15M phosphate buffer (pH 6) (15 ml). PtO$_2$ (180 mg) was added to this solution and the whole was subjected to catalytic hydrogenation under 4 atm for 45 min at room temperature, then cooled below 5°. The catalyst was removed by filtration and washed with H$_2$O. The filtrate and washings were combined, washed with CHCl$_3$ and concentrated to ca. 30 ml under reduced pressure. The residual solution was applied to Diaion-HP20 column chromatography (20×250 mm) using H$_2$O and 5% THF as eluents. The fraction eluted with 5% THF was found to contain 1-carbapenem derivative by UV assay, and further purified by HPLC to give (47A) (3.5 mg) and (47B) (3.5 mg).

(47A)
UV λ(H$_2$O): 298 nm.
IR υ(KBr): 1760, 1670, 1640, 1580 cm$^{-1}$.
NMR δ(D$_2$O): 1.29 (3H, d, J=6 Hz, CH$_3$); 1.80–2.06 (2H, m); 2.10–2.30 (2H, m); 3.11 (3H, s, NCH$_3$); 3.19–3.30 (2H, m); 3.46–3.52 (1H, m); 3.50–3.65 (2H, m); 4.20–4.40 (3H, m); 4.80 (HOD).

(47B)
UV λ(H$_2$O): 298 nm.
IR υ(KBr): 1760, 1670, 1640, 1580 cm$^{-1}$.
NMR δ(D$_2$O): 1.27 (3H, d, J=6 Hz, CH$_3$); 1.80–2.30 (4H, m); 3.06–3.22 (5H, br s, NCH$_3$ and C$_1$—H$_2$); 3.42–3.65 (3H, m); 4.10–4.35 (3H, m).

HPLC column: μ-Bondapak C$_{18}$ (7.8×300 mm); solvent: MeCN—H$_2$O=5:95 v/v; flow rate: 3 ml/min; retention time: (47A)=13.5 min, (47B)=15.4 min.

N-substituted amidinylcarbapenems such as 47 may thus be prepared as follows: N-protected amino alcohol 36 is prepared by treatment of 3-aminopropanol with BOC—ON. Protection of the alcohol function with benzoyl chloride and pyridine and N-alkylation with an alkyl halide and sodium hydride followed by alkaline solvolysis of the benzoate affords 37. Alcohol 37 is converted to tosylate 38 with tosyl chloride and pyridine, and 38 affords iodide 39 upon exposure to sodium iodide in acetone. The substituted cyanoacetate 41 is prepared by reaction of bromide 40 with p-methoxybenzyl mercaptan and triethylamine. Exposure of 41 to sodium hydride followed by iodide 39 affords coupling product 42. Decarboalkoxylation is effected by alkaline solvolysis of the ester function of 42, followed by thermal decarboxylation, affording 43. Removal of the BOC group with trifluoroacetic acid in anisole affords aminonitrile 44, which cyclizes upon heating with p-toluene sulfonic acid to yield amidine 45. Exposure of 45 to trifluoroacetic acid, trifluoromethane sulfonic acid and anisole affords free thiol 46. Addition of 46 to carbapenem sulfoxide 14 in the presence of DBU, followed by hydrogenolysis over platinum oxide affords amidinyl carbapenems 47.

EXAMPLE 5

Preparation of Pharmaceutical Compositions

One such unit dosage form consists in mixing 120 mg of Compound 34A with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules or compressed tablets and pills can also be prepared. The following examples are illustrative of the preparation of pharmaceutical formulations:

| TABLET | PER TABLET |
|---|---|
| Compound 34A | 125 mg |
| Cornstarch, U.S.P. | 6 mg |
| Dicalcium Phosphate | 192 mg |

| TABLET | PER TABLET |
| --- | --- |
| Lactose, U.S.P. | 190 mg |
| Magnesium Stearate | 287 mg |

The active ingredient is blended with the dicalcium phosphate, lactose and about half of the cornstarch. The mixture is then granulated with a 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
| --- | --- |
| Ampoule: | |
| Compound 34A | 500 mg |
| Sterile water | 2 ml |
| OPHTHALMIC SOLUTION | |
| Compound 34A | 100 mg |
| Hydroxypropylmethylcellulose | 5 mg |
| Sterile water | to 1 ml |
| OTIC SOLUTION | |
| Compound 34A | 100 mg |
| Benzalkonium Chloride | 0.1 mg |
| Sterile water | to 1 ml |
| TOPICAL OINTMENT | |
| Compound 34A | 100 mg |
| Polyethylene Glycol 4000 U.S.P. | 400 mg |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

Similarly, prepare other formulations of the present invention by substituting Compound 34B for Compound 34A in the above formulations.

What is claimed is:

1. A compound of the formula:

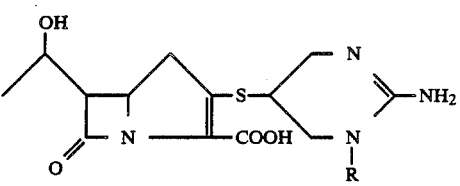

wherein R is hydrogen or alkyl of 1 to 6 carbon atoms; and the pharmaceutically acceptable salts thereof.

2. 2-[2-Amino-3,4,5,6-tetrahydropyrimidin-5-yl)thio]-6-(1-hydroxyethyl)-1-carbadethiapen-2-em-3-carboxylic acid.

3. 2-[2-Amino-1-methyl-3,4,5,6-tetrahydropyrimidin-5-yl)thio]-6-(1-hydroxyethyl)-1-carbadethiapen-2-em-3-carboxylic acid.

4. A pharmaceutical composition for treating bacterial infections comprising an antibacterially effective amount of a compound of claim 1 and a pharmaceutically acceptable carrier.

5. A method of treating bacterial infections in mammals comprising administering to a mammal in need of such treatment an antibacterially effective amount of a compound of claim 1.

* * * * *